United States Patent [19]

Yang

[11] Patent Number: 5,420,367
[45] Date of Patent: May 30, 1995

[54] POLYMERS OF VINYL(PERFLUOROCYCLOPROPANE)

[75] Inventor: Zhen-Yu Yang, Wilmington, Del.

[73] Assignee: E. I. Du Pont de Nemours and Company, Wilmington, Del.

[21] Appl. No.: 312,723

[22] Filed: Sep. 27, 1994

[51] Int. Cl.$^6$ .................. C07C 19/00; C07C 21/00
[52] U.S. Cl. .................................................. 570/133
[58] Field of Search ........................................ 570/133

[56] References Cited

U.S. PATENT DOCUMENTS

| | | | |
|---|---|---|---|
| 2,394,581 | 2/1946 | Benning et al. | 570/133 |
| 2,727,900 | 12/1955 | Shukys et al. | 570/133 |
| 3,349,136 | 10/1967 | Boudakian et al. | 570/133 |
| 3,509,197 | 4/1970 | Mitsch | 570/133 |
| 3,816,553 | 6/1974 | Smart | 570/133 |
| 3,872,066 | 3/1975 | Smart | 570/133 |
| 4,570,018 | 2/1986 | Aoki et al. | 570/133 |

FOREIGN PATENT DOCUMENTS

| | | | |
|---|---|---|---|
| 0127920 | 12/1984 | European Pat. Off. | 570/133 |
| 2141707 | 1/1985 | United Kingdom | 570/133 |

OTHER PUBLICATIONS

Sanda, F. et al, *Macromolecules*, 25, 6719–6721 (1992).
Sanda, F. et al, *Macromolecules*, 26, 5748–5754 (1993).
Sanda, F. et al, *Macromolecules*, 26, 1818–1824 (1993).

*Primary Examiner*—Joseph L. Schofer
*Assistant Examiner*—N. Sarofim

[57] ABSTRACT

Disclosed herein are polymers made by free radically polymerizing the novel compound vinyl(perfluorocyclopropane), and optionally other monomers to form copolymers. The repeat unit formed by vinyl(perfluorocyclopropane) contains an olefinic bond, making it particularly useful as a grafting and/or crosslinking site.

3 Claims, No Drawings

POLYMERS OF VINYL(PERFLUOROCYCLOPROPANE)

FIELD OF THE INVENTION

This invention concerns polymers containing repeat units derived from the free radical polymerization of the novel compound vinyl(perfluorocyclopropane).

TECHNICAL BACKGROUND

Fluorinated polymers are important items of commerce, being particularly useful in situations where heat and/or chemical resistance are required, for example in films and coatings. Therefore new fluorinated polymers and/or technology for usefully modifying "known" fluorinated polymers are constantly being sought.

Unfluorinated vinylcyclopropane and it polymers has been described in F. Sanda, et al., Macromolecules, vol. 25, p. 6719–6721 (1992); ibid., vol. 26, p. 1818–124 (1993); ibid., vol. 26, p. 5748–5754 (1993).

SUMMARY OF THE INVENTION

This invention concerns a polymer, comprising, the repeat unit $-CF_2CF_2CF=CHCH_2-$ (I).

This invention also concerns a compound of the formula

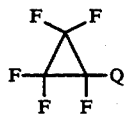

wherein Q is $-CH_2CH_2X$ or $-CH=CH_2$, wherein X is Cl, Br or I. It is preferred if X is Br.

The polymers described herein are useful for films and coatings, and the repeat unit formed by free radical polymerization of vinyl(perfluorocyclopropane) (VPCP, also sometimes called vinylpentafluorocyclopropane) is particularly useful as a crosslinking or grafting site for such polymers.

DETAILS OF THE INVENTION

The essential monomer used herein is VPCP. It is made by the procedures shown in Examples 1 and 2. It can be free radically polymerized by contact with free radicals using for instance common free radical initiators, including, but not limited to, bis(perfluoropropionyl) peroxide, benzoyl peroxide, potassium persulfate and persulfate-bisulfite redox pair.

The polymerizations may be carried out in any conventional way, for example, solution, aqueous dispersion or emulsion, organic emulsion or neat. They may be done batch, continuous and semibatch, see, for instance, polymerization methods described in H. Mark, et al., Ed., Encyclopedia of Polymer Science and Engineering, vol. 16, John Wiley & Sons, New York, 1989, p. 577–648. Suitable organic solvents or dispersants include halocarbons such as 1,1,2-trichloro-1,2,2-trifluorethane (CFC113), perfluoroethers such as perfluorotetrahydrofuran, and perfluorosulfides.

The VPCP may be polymerized by itself to form a homopolymer, or may be copolymerized with other monomers to form copolymers. Suitable comonomers include tetrafluoroethylene, perfluoro(2,2-dimethyl-1,3-dioxole), perfluoro(propyl vinyl ether), perfluoro(methyl vinyl ether), chlorotrifluoroethylene, vinylidene fluoride, hexafluoropropylene, and vinyl fluoride. Preferred comonomers are tetrafluoroethylene, perfluoro(2,2-dimethyl-1,3-dioxole), and perfluoro(alkyl vinyl ether), and tetrafluoroethylene is especially preferred. Particularly preferred copolymers are elastomeric copolymers containing VPCP, hexafluoropropylene, vinylidene fluoride, and optionally tetrafluoroethylene. By "comprising" herein it is meant that the polymer contains the repeat unit derived from VPCP plus any other repeat units. Copolymers are preferred polymers of VPCP.

The repeat unit that the VPCP produces by the polymerization is $-CF_2CF_2CF=CHCH_2-$, which contains an olefinic bond. This olefinic bond is reactive towards nucleophiles, and so may react with suitable nucleophiles to form a graft polymer. If a di- or higher functionality compound (containing two or more nucleophilic reactive groups) is used, the polymer will be crosslinked. This makes VPCP particularly valuable as a curesite monomer in elastomers, especially those which are (partially) fluorinated and can now be cured through double bonds which are present or are generated. Such copolymers include those of vinylidene fluoride and hexafluoropropylene, optionally also containing tetrafluoroethylene, and the copolymer of tetrafluoroethylene and propylene. Since curesite monomers are often present in elastomers in relatively low concentrations, in one preferred embodiment the repeat unit from VPCP (I) is about 0.2 to about 5 mole percent of the total number of repeat units present in the polymer.

In DSC determinations, the instrument used was a DuPont DSC 2190, with a heating rate of 20° C./min, and the maximum of the endotherm was taken as the melting point.

In the Examples, the following abbreviations are used:

DMF—N,N-dimethylformamide
DMSO—dimethylsulfoxide
DSC—differential scanning calorimetry
FC-75—perfluorobutyltetrahydrofuran
PTFE—polytetrafluoroethylene
TGA—thermogravimetric analysis

EXAMPLE 1

Preparation of 2-bromo-1-(pentafluorocyclopropyl)ethane

A 300 mL shaker tube was charged with 65 g of $CF_2=CFCH_2CH_2Br$ and 114 g of hexafluoropropylene oxide and heated at 200° C. for 9 hrs. Crude product (80.3 g) was distilled to give 8.6 g of bp 95.6°–106° C. materials and 1.2 g of bp 107° to 111° C. materials which contained 16% starting material $CF_2=CFCH_2CH_2Br$. Further distillation on a spinning band gave 41.3 g of pure 2-bromo-1-(pentafluorocyclopropyl(ethane), bp 111° to 112° C. $^{19}F$ NMR: $-152.5$ (dr, J=197 Hz, J=7.2 Hz, 2F), $-157.1$ (dm, J=197 Hz, 2H), $-212.3$ (tt, J=21.5 Hz, J=7.1 Hz, 1F). $^1H$ NMR: 3.53 (t, J=7.1 Hz, 2H), 2.55 (dm, J=21.5 Hz, 2H).

EXAMPLE 2

Preparation of vinylpentafluorocyclopropane

To a stirred solution of 18.0 g of KOH, 15 mL of ethanol and 20 mL of water was slowly added 24.0 g of 2-bromo-1-(pentafluorocyclopropyl)ethane at 70° C. During the addition, volatiles were collected in a $-78°$ C. trap. After the addition was complete, the reaction mixture was stirred at 70° C. for an additional two hours until collection of all volatiles, which was distilled to give 9.1 g of product, bp 30° C. $^{19}$F NMR: −152.3 (dt, J=195.4 Hz, J=9.8 Hz, 2F), −156.0 (dm, J=195.6 Hz, 2F), −210.7 (t, J=7.7 Hz, 1F). $^1$H NMR: 5.86–5.73 (m, 2H), 5.70–5.65 (m, 1H).

EXAMPLE 3

Homopolymerization of vinylpentafluorocyclopropane

A 25 mL glass ampul fitted with a PTFE coated stir bar was charged with 0.3 mL of 5% of bis(perfluoropropionyl) peroxide in 1,1,2-trichlorotrifluoroethane and 1.1 g of the title compound. The ampul was sealed and cooled in a liquid nitrogen bath. After being evacuated and purged with N$_2$ alternately six times, contents of the sealed ampul were stirred at 40° C. for 4 hours. The white solids were washed with acetone and dried under vacuum at 125° C. to give 1.1 g of polymer.

The IR spectrum of this polymer showed an absorption at 1719 cm$^{-1}$ which could be attributed to double bonds in the polymer.

This polymer was insoluble in acetone, ethyl acetate, tetrahydrofuran, acetonitrile, DMSO, DMF, hexafluorobenzene and FC-75. The polymer had a melting point of 130° C. by DSC (second heat). By TGA the polymer showed 10% weight loss temperatures of about 400° C. in nitrogen and 375° C. in air when heated at 20° C./minute.

EXAMPLE 4

Comopolymerization of vinylpentafluorocyclopropane with perfluoropropyl vinyl ether (PPVE)

A 25 mL glass ampul fitted with a PTFE coated stir bar was charged with 0.3 mL of 5% of bis(perfluoropropionyl) peroxide in 1,1,2-trichlorotrifluoroethane and 1.1 g of the title compound and 1.0 g of PPVE. The ampul was sealed and cooled in a liquid nitrogen bath. After being evacuated and purged with N$_2$ alternately six times, contents of the sealed ampul were stirred at 40° C. for 18 hours. The white solids were washed with CFC113 and dried under vacuum at 125° C. to give 0.9 g of polymer.

This polymer was insoluble in acetone, ethyl acetate, tetrahydrofuran, acetonitrile, DMSO, DMF, hexafluorobenzene and FC-75. The polymer had a melting point of 131° C. by DSC (second heat). By TGA the polymer showed 10% weight loss temperatures of about 405° C. in nitrogen and 370° C. in air when heated at 20° C./minute.

EXAMPLE 5

Comopolymerization of vinylpentafluorocyclopropane perfluoro-2,2-dimethyl-1,3-dioxole (PDD)

A 25 mL glass ampul fitted with a PTFE coated stir bar was charged with 0.3 mL of 5% of bis(perfluoropropionyl) peroxide in 1,1,2-trichlorotrifluoroethane and 1.0 g of the title compound and 1.0 g of PDD. The ampul was sealed and cooled in a liquid nitrogen bath. After being evacuated and purged with N$_2$ alternately six times, contents of the sealed ampul were stirred at 40° C. for 18 hours. The white solids were washed with CFC113 and dried under vacuum at 125° C. to give 0.9 g of polymer.

This polymer was insoluble in acetone, ethyl acetate, tetrahydrofuran, acetonitrile, DMSO, DMF, hexafluorobenzene and FC-75. The polymer had a melting point of 127.5° C. by DSC (second heat). By TGA the polymer showed 10% weight loss temperatures of about 395° C. in nitrogen and 355° C. in air when heated at 20° C./minute.

EXAMPLE 6

Comopolymerization of vinylpentafluorocyclopropane with chlorotrifluoroethylene(CTFE)

A 25 mL glass ampul fitted with a PTFE coated stir bar was charged with 0.3 mL of 5% of bis(perfluoropropionyl) peroxide in 1,1,2-trichlorotrifluoroethane, 1.0 g of the title compound, 1.0 g of CTFE and 2 mL of CFC113. The ampul was sealed and cooled in a liquid nitrogen bath. After being evacuated and purged with N$_2$ alternately six times, contents of the sealed ampul were stirred at 40° C. for 72 hours. The white solids were filtered, washed with CFC113 and dried under vacuum at 125° C. to give 0.15 g of polymer.

This polymer was insoluble in acetone, ethyl acetate, tetrahydrofuran, acetonitrile, DMSO, DMF, hexafluorobenzene and FC-75. The polymer had a melting point of 127° C. by DSC (second heat). By TGA the polymer showed 10% weight loss temperatures of about 400° C. in nitrogen and 355° C. in air when heated at 20° C./minute.

What is claimed is:

1. A compound of the formula

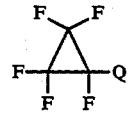

wherein Q is —CH$_2$CH$_2$X or —CH=CH$_2$, wherein X is Cl, Br or I.

2. The compound as recited in claim 1 wherein Q is —CH=CH$_2$.

3. The compound as recited in claim 1 wherein Q is —CH$_2$CH$_2$Br.

* * * * *